(12) United States Patent
Kim et al.

(10) Patent No.: US 6,610,185 B2
(45) Date of Patent: Aug. 26, 2003

(54) ELECTROCHEMICAL CORROSION POTENTIAL SENSOR AND METHOD OF MAKING

(75) Inventors: Young-Jin Kim, Clifton Park, NY (US); Reed Roeder Corderman, Niskayuna, NY (US); Peter Louis Andresen, Schenectady, NY (US); Scott Andrew Weaver, Ballston Lake, NY (US); Paul Joseph Martiniano, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/682,725

(22) Filed: Oct. 10, 2001

(65) Prior Publication Data
US 2003/0132111 A1 Jul. 17, 2003

(51) Int. Cl.[7] ............................................. G01N 27/26
(52) U.S. Cl. ........................... 204/404; 29/428; 29/460; 29/592.1; 29/DIG. 4; 204/400; 205/775.5; 324/700; 376/245; 376/305
(58) Field of Search ................................. 204/400, 404, 204/435; 205/775, 775.5–777; 376/245, 305; 324/700, 724; 29/428, 460, 592.1, DIG. 4

(56) References Cited

U.S. PATENT DOCUMENTS

| | | | |
|---|---|---|---|
| 5,217,596 A | | 6/1993 | Indig et al. |
| 5,516,413 A | * | 5/1996 | Foster et al. |
| 5,571,394 A | | 11/1996 | Hettiarachchi et al. |
| 5,848,113 A | | 12/1998 | Kim et al. |
| 5,896,432 A | | 4/1999 | Kim et al. |
| 6,181,760 B1 | | 1/2001 | Kim et al. |
| 6,370,213 B1 | * | 4/2002 | Kim et al. |

OTHER PUBLICATIONS

US Patent Application Ser. #09/397,840, Filed Sep. 17, 1999 (RD–26,996), Kim, et al.

* cited by examiner

Primary Examiner—T. Tung
(74) Attorney, Agent, or Firm—Paul J. DiConza; Patrick K. Patnode

(57) ABSTRACT

A sensor for measuring electrochemical corrosion potential, and a method for manufacturing a sensor, the sensor comprising a tubular ceramic probe having a closed tip at one end, the probe at least partially filled with a powder comprising metal and metal oxide; a metal support tube having one end receiving an opposite end of the probe, and joined thereto by a braze joint therewith; an electrical conductor extending through the support tube and into the probe, and having an end buried in the powder for electrical contact therewith; and a protective band bridging the probe and tube at the joint for sealing thereof, the protective band consisting essentially of a metallic coating.

30 Claims, 1 Drawing Sheet

ELECTROCHEMICAL CORROSION POTENTIAL SENSOR AND METHOD OF MAKING

BACKGROUND OF INVENTION

This invention relates to electrochemical sensors. More particularly, this invention relates to sensors for determination of electrochemical corrosion potential (ECP) of metal components in liquids at high temperatures and pressures. This invention also relates to methods for making electrochemical corrosion potential sensors.

Many areas of industry, such as, for example, the power generation industry, employ metal structural components that are exposed to liquids at high temperatures and pressures. Examples of systems in which equipment is designed for such exposure include nuclear reactors, including the boiling water and pressurized water reactor types; fossil fuel systems; and geothermal systems. In a boiling water nuclear reactor, for example, water and steam are channeled through various conduits formed of stainless steel. Normal water chemistry conditions include high oxidizing species, such as oxygen and hydrogen peroxide, which may lead to intergranular stress corrosion cracking (IGSCC) of the stainless steel.

IGSCC can be mitigated by lowering the concentrations of ionic impurities and oxidizing species in the reactor water. In a nuclear reactor, for example, this lowering of impurity concentration may be effected using hydrogen water chemistry (HWC) in which hydrogen is added to the feed water of the reactor. The primary purpose of the added hydrogen is to reduce the dissolved oxidant concentrations and thereby lower the ECP below a critical value at which IGSCC susceptibility is significantly reduced.

Various forms of ECP sensors are used for measuring ECPs in nuclear reactors and other systems. The sensors have different configurations for measuring ECPs, and are subject to different problems that limit their useful lives. For a nuclear reactor, for example, the useful life of a sensor should cover the duration of at least a single fuel cycle, which is typically in the range from about 18 months to about 24 months in the United States. However, experience in actual nuclear reactors has demonstrated sensor failure in a shorter duration due to various causes.

One type of ECP sensor, disclosed in U.S. patent application Ser. No. 09/397,840, now U.S. Pat. No. 6,370,213 commonly owned by the present assignee, includes a ceramic probe in which is packed a mixture of metal and metal oxide powder for providing a corresponding reference ECP. This mixture may include iron and iron oxide (Fe/$Fe_3O_4$), or copper and copper oxide (Cu/$Cu_2O$), or nickel and nickel oxide (Ni/NiO).

In this type of sensor, the probe is typically in the form of a zirconia tube brazed to a support tube made of a suitable metal such as INVAR™ low-expansion alloy with a nominal composition of 36% by weight nickel, 64% by weight iron, and <1% other additions, or other alloy with a suitably low thermal expansion such as, for example, alloy 42, with a nominal composition of 42% by weight nickel, balance iron. This support tube in turn is often welded to a stainless steel tube. An electrical conductor extends through the tubes into the probe and is buried in the operative mixture.

In one example, the ceramic probe is formed of magnesia-stabilized-zirconia (MSZ) brazed to an alloy 42 support tube. Since the ceramic probe and metal tube have different coefficients of thermal expansion, they are subject to thermal shock during high temperature operation which can lead to cracking of the braze joint.

The braze material is also subject to corrosion during operation. Both problems potentially limit the useful life of the sensor, because failure of the braze joint causes water leakage inside the sensor and failure thereof.

To address these problems, the aforementioned U.S. patent application Ser. No. 09/397,840 discloses and claims an ECP sensor designed to mitigate degradation of this braze joint by employing a ceramic band, often applied via plasma spraying, selectively applied around the perimeter of the sensor for bridging the probe and support tube at the braze joint for covering and sealing thereof. Although such a band provides improved protection for the sensor, plasma sprayed ceramics may occasionally exhibit undesirable levels of porosity, which may affect the ability of the ceramic to provide a barrier against corrosion.

Accordingly, it is desired to provide an ECP sensor with improvements addressing these problems.

SUMMARY OF INVENTION

Embodiments of the present invention are provided to address the issue of ECP sensor reliability. One embodiment provides a sensor for measuring electrochemical corrosion potential comprising: a tubular ceramic probe having a closed tip at one end, the probe at least partially filled with a powder comprising metal and metal oxide; a metal support tube having one end receiving an opposite end of the probe, and joined thereto by a braze joint therewith; an electrical conductor extending through the support tube and into the probe, and having an end buried in the powder for electrical contact therewith; and a protective band bridging the probe and tube at the joint for sealing thereof, the protective band consisting essentially of a metallic coating. A second embodiment provides a method for manufacturing a sensor for measuring electrochemical corrosion potential, the method comprising: providing a tubular ceramic probe having a closed tip at one end, the probe at least partially filled with a powder comprising metal and metal oxide; providing a metal support tube having one end receiving an opposite end of the probe; joining the tube with the probe by forming a braze joint therewith; and depositing a protective band bridging the probe and tube at the joint for sealing thereof, the protective band consisting essentially of a metallic coating.

BRIEF DESCRIPTION OF DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
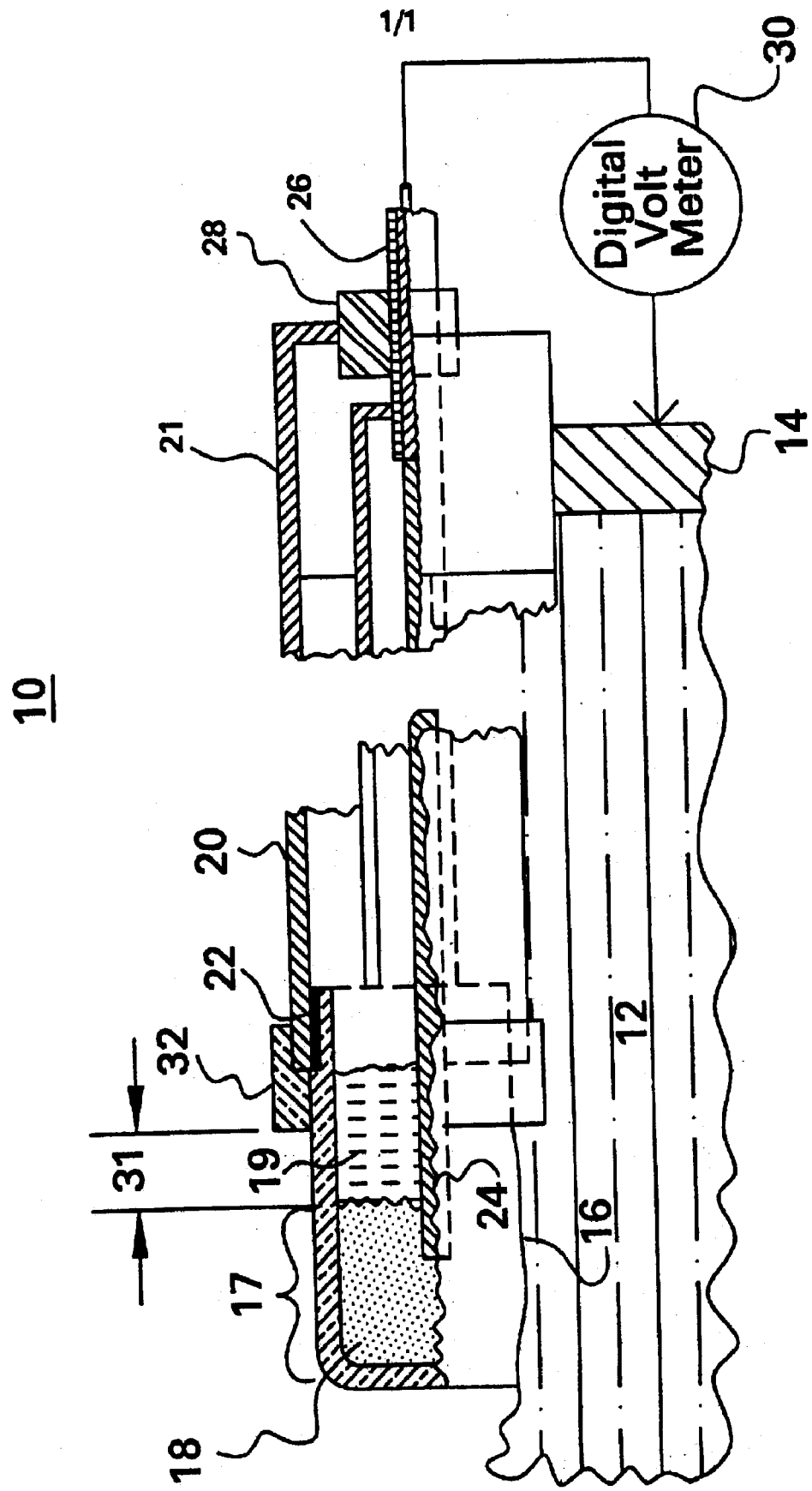
FIG. 1 is a cross-sectional schematic representation of an ECP sensor shown in relevant portion of a structural component in accordance with an exemplary embodiment of the present invention.

Illustrated schematically in FIG. 1 is an ECP sensor 10 configured for measuring electrochemical corrosion potential of component surfaces in circulating liquid 12, such as, for example, water, inside a component 14, such as, for example, the pressure vessel of a conventional boiling water nuclear reactor, shown in relevant part.

The sensor comprises a tubular ceramic probe 16 having a closed tip 17 at one end of the probe 16, the probe 16 at least partially filled with a dry powder 18 comprising metal and metal oxide. The powder 18 is contained within the probe 16 by a packing material 19, such as, for example, glass wool. The probe tip 17 is considered to extend from the closed end of the ceramic probe 16 to the interface between the powder 18 and the packing material 19.

A metal support tube 20 has a distal end receiving an opposite end of the probe 16 for support thereof, and is joined thereto by a braze joint 22 therewith. Materials suitable for the construction of the support tube 20 include alloy 42, for example, and examples of suitable braze joint 22 materials include alloys comprising at least one of silver, copper, and titanium, which are conventionally used to join ceramic to metal. In certain embodiments, a proximal end of said support tube 20 is typically welded coaxial with a distal end of a secondary support tube 21 typically formed of stainless steel.

An electrical conductor 24 extends through the support tubes 20, 21 and into the probe 16, and has an end buried in the powder 18 for electrical contact therewith. The material used to form the conductor 24 often comprises a pure metal of the same element employed in the powder 18. For example, where an embodiment employs a powder 18 comprising nickel and nickel oxide, the conductor often comprises nickel. A coaxial electrical cable 26 extends through a suitable sealing collar 28 at a proximal end of the secondary tube 21 and is suitably joined to the electrical conductor 24 inside the sensor. The cable 26 is suitably routed to a digital voltmeter 30 with a sufficiently high input impedance, generally at least about $10^9$ ohms, for measuring electrochemical corrosion potential.

In embodiments of the present invention, a protective band 32 is selectively applied around the perimeter of the sensor, bridging the probe 16 and support tube 20 at the braze joint 22 for sealing thereof, the protective band 32 consisting essentially of a metallic coating.

In certain embodiments, the band 32 locally coats the probe 16 and support tube 20 at the braze joint 22 such that the probe tip 17 is uncoated by the band 32. In particular embodiments, the band 32 locally coats the probe 16 and support tube 20 at the braze joint 22 such that the probe tip 17 and a portion of the probe 16 are uncoated by the band 32. In more particular embodiments, the portion of the probe 16 uncoated by the band 32 has a length 31 of at least about 5 mm, and in specific embodiments, the length 31 is at least about 10 mm. Spacing the band 32 from the probe tip 17 ensures that possible electrochemical interactions between the powder 18 and the metallic band 32, which could adversely affect the performance of the sensor 10, are kept to a minimum.

The ceramic probe 16 comprises zirconia in certain embodiments of the present invention, and in particular embodiments the probe 16 comprises at least one of magnesia-stabilized-zirconia (MSZ) and yttria-stabilized-zirconia (YSZ), both of which have different coefficients of thermal expansion than that of the metal support tube 20, and that of the braze joint 22.

In embodiments of the present invention, particularly those embodiments in which the ECP sensor 10 is designed for use in nuclear reactors, the selection of suitable metals to be used in forming the band 32 considers a variety of factors, including, for example, not only corrosion resistance and cost, but also a material's potential to form radioactive isotopes during service exposure. In certain embodiments, the metallic coating comprises at least one element selected from the group consisting of scandium, titanium, vanadium, zirconium, niobium, yttrium, lanthanum, hafnium, and tantalum. In particular embodiments the metallic coating comprises at least one metal selected from the group consisting of a tantalum alloy, a zirconium alloy, a nickel alloy, a stainless steel, and a titanium alloy. Such materials exhibit corrosion resistance in environments typical of a boiling water reactor sufficient to afford desired levels of protection to the braze joint 22. For example, several zirconium alloys, such as, for example, those commonly known in the art as Zircaloy-2 and Zircaloy-4, and another alloy comprising a nominal composition of about 2.5% by weight niobium, balance zirconium (herein referred to as "Zr-2.5Nb"), have proven to be resistant to high-temperature, high-flow water under high radiation environments. In particular embodiments of the present invention, the metallic coating comprises at least one zirconium alloy selected from the group consisting of Zircaloy-2, Zircaloy-4, and Zr-2.5Nb.

In one embodiment, the protective band 32 comprises a coating selected from the group consisting of a thermal-sprayed coating, a plasma-sprayed coating, a high-velocity oxy-fuel (HVOF) sprayed coating, a chemical vapor deposited (CVD) coating, a physical vapor deposited (PVD) coating, an electroplated coating, an electroless-plated coating, and an electrophoretic coating. The band 32 thusly provides an intimate bond with the probe 16 and support tube 20 for providing an effective seal at the braze joint 22.

The thickness of the band 32 selected for a particular embodiment depends in part upon the particular process employed to deposit the coating. For example, a plasma-sprayed coating typically comprises a level of porosity that is higher than that of coatings deposited by the other processes identified above, and as a result coatings deposited by plasma spray for embodiments of the present invention often are deposited at higher thickness, for example, a thickness in the range from about 0.03 mm to about 0.3 mm, than coatings deposited by other processes, to ensure that the coating exhibits desired levels of protection. The advantageously high-density coatings provided by processes exemplified by CVD, PVD, HVOF, and electroplating allow for effective protection of the braze joint 22 by coatings as thin as about 1 μm for certain embodiments where these processes are applied. The aggressiveness of the environment also has a part in determining desirable thickness for the band 32. Factors for consideration include, but are not limited to, impurity levels, temperature, flow rate, radiation level, and oxidizing conditions. The desired thickness of the band 32 is generally increased for more highly aggressive exposure conditions.

Embodiments of the present invention are provided for which various alternative materials are used in making the powder 18. In one embodiment, the powder 18 comprises iron and iron oxide ($Fe/Fe_3O_4$), In other embodiments, the powder 18 comprises copper and copper oxide. In other embodiments, the powder 18 comprises nickel and nickel oxide. The reference potential of the sensor varies depending upon the particular composition of the powder 18.

Other embodiments of the present invention provide a method for manufacturing a sensor 10 for measuring electrochemical corrosion potential. The method comprises: providing a tubular ceramic probe 16 having a closed tip 17 at one end, the probe 16 at least partially filled with a powder 18 comprising metal and metal oxide; providing a metal support tube 20 having one end receiving an opposite end of the probe 16; joining the tube 20 with the probe 16 by forming a braze joint 22 therewith; and depositing a protective band 32 bridging the probe 16 and the tube 20 at the joint 22 for sealing thereof, the protective band 32 consisting essentially of a metallic coating. Examples of suitable materials for the composition of the probe 16, the powder 18, the support tube 20, the braze, and the band 32 are the same as those examples described above for the sensor 10.

In certain embodiments, depositing the protective band 32 comprises locally applying the coating to the probe 16 and the tube 20 at the braze joint 22 such that the probe tip 17 is uncoated by the band 32.

In particular embodiments, depositing the protective band comprises applying the coating by a process selected from the group consisting of plasma spraying, high-velocity oxy-fuel (HVOF) spraying, chemical vapor deposition, physical vapor deposition, electroless plating, electrophoretic deposition, and electroplating. In certain embodiments, the band 32 is sprayed to a thickness in the range described above for the sensor 10.

While various embodiments are described herein, it will be appreciated from the specification that various combinations of elements, variations, equivalents, or improvements therein may be made by those skilled in the art, and are still within the scope of the invention as defined in the appended claims.

What is claimed is:

1. A sensor for measuring electrochemical corrosion potential comprising:
   a tubular ceramic probe having a closed tip at one end, said probe at least partially filled with a powder comprising metal and metal oxide;
   a metal support tube having one end receiving an opposite end of said probe, and joined thereto by a braze joint therewith;
   an electrical conductor extending through said support tube and into said probe, and having an end buried in said powder for electrical contact therewith; and
   a protective band bridging said probe and tube at said joint for sealing thereof, said protective band consisting essentially of a metallic coating.

2. A sensor according to claim 1, wherein said band locally coats said probe and said tube at said braze joint, such that said probe tip is uncoated by said band.

3. A sensor according to claim 2, wherein said band locally coats said probe and support tube at said braze joint such that said probe tip and a portion of said probe are uncoated by said band.

4. A sensor according to claim 3, wherein said portion of said probe has a length of at least about 5 mm.

5. A sensor according to claim 4, wherein said length is at least about 10 mm.

6. A sensor according to claim 2, wherein said probe comprises zirconia.

7. A sensor according to claim 6, wherein said probe comprises at least one of magnesia-stabilized-zirconia and yttria-stabilized-zirconia.

8. A sensor according to claim 2, wherein said powder comprises iron and iron oxide.

9. A sensor according to claim 2, wherein said powder comprises copper and copper oxide.

10. A sensor according to claim 2, wherein said powder comprises nickel and nickel oxide.

11. A sensor according to claim 2, wherein said metallic coating comprises at least one element selected from the group consisting of scandium, titanium, vanadium, zirconium, niobium, yttrium, lanthanum, hafnium, and tantalum.

12. A sensor according to claim 2, wherein said metallic coating comprises at least one metal selected from the group consisting of a tantalum alloy, a zirconium alloy, a nickel alloy, a stainless steel, and a titanium alloy.

13. A sensor according to claim 12 wherein said metallic coating comprises at least one zirconium alloy selected from the group consisting of Zircaloy-2, Zircaloy-4, and Zr-2.5Nb.

14. A sensor according to claim 2, wherein said band comprises a coating selected from the group consisting of a plasma sprayed coating, high-velocity oxy-fuel (HVOF) sprayed coating, a chemical vapor deposited coating, a physical vapor deposited coating, an electroplated coating, an electroless-plated coating, and an electrophoretic coating.

15. A sensor for measuring electrochemical corrosion potential comprising:
    a tubular ceramic probe comprising zirconia and having a closed tip at one end, said probe at least partially filled with a powder comprising iron and iron oxide;
    a metal support tube having one end receiving an opposite end of said probe, and joined thereto by a braze joint therewith;
    an electrical conductor extending through said support tube and into said probe, and having an end buried in said powder for electrical contact therewith; and
    a protective band bridging said probe and tube at said joint for sealing thereof, said protective band consisting essentially of a metallic coating, said coating comprising at least one metal selected from the group consisting of a tantalum alloy, a zirconium alloy, a nickel alloy, a stainless steel, and a titanium alloy, wherein said band locally coats said probe and said tube at said braze joint, such that said probe tip is uncoated by said band.

16. A method for manufacturing a sensor for measuring electrochemical corrosion potential, said method comprising:
    providing a tubular ceramic probe having a closed tip at one end, said probe at least partially filled with a powder comprising metal and metal oxide;
    providing a metal support tube having one end receiving an opposite end of said probe;
    joining said tube with said probe by forming a braze joint therewith; and
    depositing a protective band bridging said probe and said tube at said joint for sealing thereof, said protective band consisting essentially of a metallic coating.

17. The method of claim 16, wherein depositing said protective band comprises locally applying said coating to said probe and said tube at said braze joint such that said probe tip is uncoated by said band.

18. The method of claim 17, wherein depositing said protective band comprises locally applying said coating to said probe and support tube at said braze joint such that said probe tip and a portion of said probe are uncoated by said band.

19. The method of claim 18, wherein said portion of said probe has a length of at least about 5 mm.

20. A sensor according to claim 19, wherein said length is at least about 10 mm.

21. The method of claim 17, wherein said probe comprises zirconia.

22. The method of claim 21, wherein said probe comprises at least one of magnesia-stabilized-zirconia and yttria-stabilized-zirconia.

23. The method of claim 17, wherein said powder comprises iron and iron oxide.

24. The method of claim 17, wherein said powder comprises copper and copper oxide.

25. The method of claim 17, wherein said powder comprises nickel and nickel oxide.

26. The method of claim 17, wherein said metallic coating comprises at least one element selected from the group consisting of scandium, titanium, vanadium, zirconium, niobium, yttrium, lanthanum, hafnium, and tantalum.

27. The method of claim 17, wherein said metallic coating comprises at least one metal selected from the group consisting a tantalum alloy, a zirconium alloy, a nickel alloy, a stainless steel, and a titanium alloy.

28. The method of claim 27, wherein said metallic coating comprises at least one zirconium alloy selected from the group consisting of Zircaloy-2, Zircaloy-4, and Zr-2.5Nb.

29. The method of claim 17, wherein depositing said protective band comprises applying said coating by a process selected from the group consisting of plasma spraying, high-velocity oxy-fuel (HVOF) spraying, chemical vapor deposition, physical vapor deposition, electroless plating, electrophoretic deposition, and electroplating.

30. A method for manufacturing a sensor for measuring electrochemical corrosion potential, said method comprising:

provided a tubular ceramic probe comprising zirconia and having a closed tip at one end, said probe at least partially filled with a powder comprising metal and metal oxide;

providing a metal support tube having one end receiving an opposite end of said probe;

joining said tube with said probe by forming a braze joint therewith; and depositing a protective band bridging said probe and said tube at said joint for sealing thereof, said protective band consisting essentially of a metallic coating, wherein depositing said protective band comprises applying said coating by a process selected from the group consisting of plasma spraying, high-velocity oxy-fuel (HVOF) spraying, chemical vapor deposition, physical vapor deposition, electroless plating, electrophoretic deposition, and electroplating, said metallic coating comprising at least one metal selected from the group consisting of a tantalum alloy, a zirconium alloy, a nickel alloy, a stainless steel, and a titanium alloy, wherein depositing said protective band further comprises locally applying said coating to said probe and said tube at said braze joint such that said probe tip is uncoated by said band.

* * * * *